US008709828B2

(12) United States Patent
Andersson et al.

(10) Patent No.: US 8,709,828 B2
(45) Date of Patent: Apr. 29, 2014

(54) METHOD FOR THE ANALYSIS OF SOLID OBJECTS

(75) Inventors: Karl Andersson, Uppsala (SE); Magnus Malmqvist, Uppsala (SE)

(73) Assignee: Ridgeview Diagnostics AB, Uppsala (SE)

( * ) Notice: Subject to any disclaimer, the term of this patent is extended or adjusted under 35 U.S.C. 154(b) by 323 days.

(21) Appl. No.: 13/049,316

(22) Filed: Mar. 16, 2011

(65) Prior Publication Data

US 2011/0195434 A1 Aug. 11, 2011

Related U.S. Application Data

(63) Continuation of application No. PCT/SE2009/051002, filed on Sep. 8, 2009.

(30) Foreign Application Priority Data

Sep. 19, 2008 (SE) ..................................... 0802000
Sep. 22, 2008 (SE) ..................................... 0802008

(51) Int. Cl.
*G01N 33/543* (2006.01)

(52) U.S. Cl.
USPC .......................................................... 436/518

(58) Field of Classification Search
None
See application file for complete search history.

(56) References Cited

U.S. PATENT DOCUMENTS

| 5,318,958 | A | * | 6/1994 | Kisilevsky ..................... 514/7.4 |
| 2004/0059519 | A1 | * | 3/2004 | Chandler et al. ................ 702/19 |
| 2006/0105390 | A1 | | 5/2006 | Zhang et al. | |
| 2009/0219012 | A1 | * | 9/2009 | Nieuwenhuis et al. ....... 324/204 |

FOREIGN PATENT DOCUMENTS

| CN | 1922483 A | 2/2007 |
| CN | 101203756 A | 6/2008 |
| WO | WO 2005/080967 | 9/2005 |
| WO | WO 2008/088288 | 7/2008 |

OTHER PUBLICATIONS

Communication (First Office Action) dated Mar. 12, 2013 issued in related Chinese Patent Application No. 200980146162.3 and English language translation thereof (22 pages).
Supplementary European Search Report dated Feb. 1, 2012 issued by the European Patent Office in related European Patent Application No. EP 09 81 4846 (10 pages).
Björke H et al., "Measuring the affinity of a radioligand with its receptor using a rotating cell dish with in situ reference area," Applied Radiation and Isotopes, Elsevier, Oxford, Great Britain, vol. 64; No. 1, Jan. 2006 (6 pages).
Björke H et al., "Automated, high-resolution cellular retention and uptake studies in vitro," Applied Radiation and Isotopes, Elsevier, Oxford, Great Britain, vol. 64, No. 8, Aug. 1, 2006 (5 pages).
Hanna Björkelund et al., "Gefitinib Induces Epidermal Growth Factor Receptor Dimers Which Alters the Interaction Characteristics with 125I-EGF," PLOS ONE, vol. 6, No. 9, E24739, Sep. 12, 2011, Public Library of Science, San Francisco, California ( 11 pages).
International Search Report mailed Dec. 18, 2009 issued by the International Searching Authority in priority application PCT/SE2009/051002 (6 pages).
International Preliminary Report on Patentability for International Application No. PCT/SE2009/051002 dated Oct. 29, 2010 (8 pages).
Written Opinion of the International Searching Authority for International Application No. PCT/SE2009/051002 mailed Dec. 18, 2009 (8 pages).
Svitel, Juraj, et al., "Combined Affinity and Rate Constant Distributions of Ligand Populations from Experimental Surface Binding Kinetics and Equilibria," Biophysical Journal, Rockville, Md., vol. 8, Jun. 2003, pp. 4062-4077 (16 pages).
Press, Michael F., et al., "Diagnostic Evaluation of HER-2 as a Molecular Target: An Assessment of Accuracy and Reproducibility of Laboratory Testing in Large, Prospective, Randomized Clinical Trials," Clinical Cancer Research, American Association for Cancer Research, Philadelphia, PA.,vol. 11 (18), Sep. 15, 2005, pp. 6598-6607 (11 pages).
Khomyakova, Elena, et al., "On-chip hybridization kinetics for optimization of gene expression experiments," BioTechniques, Informa Bio Sciences, New York, NY., vol. 44; No. 1, 2008, pp. 109-117 (9 pages).
Gown, Alan M., "Current Issues in ER and HER2 testing by IHC in breast cancer," Modern Pathology, United States and Canadian Academy of Pathology, Augusta, GA., May 2008, vol. 21 Suppl. 2; pp. S8-S15 (8 pages).
Nestor, Marika et al., "Characterization of $^{111}$ and $^{177}$ Lu-labeled antibodies binding to CD44v6 using a novel automated radioimmunoassay," Abstract Only, Journal of Molecular Recognition, John Wiley & Sons, Inc., Malden, MA., vol. 21, pp. 179-213 (2 pages).
English language translation of "Notice of Reasons for Rejection" dated Feb. 26, 2013 issued by the Japanese Patent Office in related Japanese Patent Application No. JP 2011-527775 (2 pages).
Nestor, Marika et al., "Characterization of $^{111}$ in and $^{177}$ Lu-labeled antibodies binding to CD44v6 using a novel automated radioimmunoassay," Abstract Only, Journal of Molecular Recognition, John Wiley & Sons, Inc., Malden, MA., vol. 21, pp. 179-183 (5 pages).

(Continued)

*Primary Examiner* — Ann Lam
(74) *Attorney, Agent, or Firm* — Lucas & Mercanti LLP; Robert P. Michal (57) ABSTRACT

A method of analysis or diagnosis of solid objects is based on real-time detection of how predefined probes interact with structures present on or in the solid object combined with the calculation of how the recorded binding curves of said probes are distributed in terms of interaction properties. The interaction properties are input to a classification algorithm which automatically determines statues of the solid object. The method is particularly advantageous for solid biological objects like tissue slices combined with antibody probes, said antibody recognizing receptors known to be over-expressed in disease states on said tissue slice.

12 Claims, 7 Drawing Sheets

(56) References Cited

OTHER PUBLICATIONS

Orthogonal polynomials http://en.wikipedia.org/wiki/Category:Orthogonal_polynomials printed Nov. 9, 2013 (7 Pages).

Gedda L. et al., "Evaluation of Real-Time Immunohistochemistry and Interaction Map as an Alternative Objective Assessment of HER2 Expression in Human Breast Cancer Tissue," Research Article, Applied Immunohistochem Mol Morphol, vol. 00, No. 00, Nov. 2013, Stockholm, Sweden, (9 pages).

Kaufman, E.N. et al., "Effect of Bivalent Interaction upon Apparent Antibody Affinity: Experimental Confirmation of Theory Using Fluorescence Photobleaching and Implications for Antibody Binding Assay," Cancer Research, 1992; 52: 4157-4167, Nov. 6, 2013 American Association for Cancer Research (12 pages).

* cited by examiner

METHOD FOR THE ANALYSIS OF SOLID OBJECTS

CROSS-REFERENCE TO RELATED APPLICATIONS

This is a Continuation application of PCT International Application No. PCT/SE2009/051002 filed Sep. 8, 2009, which claims priority from Swedish Application No. 0802000-0 filed Sep. 19, 2008 and Swedish Application No. 0802008-3 filed Sep. 22, 2008, the entire disclosure of each of which is incorporated herein by reference.

FIELD OF INVENTION

The present invention relates to the field of analysis of solid objects used for analytical or diagnostic purposes. More in particular, it relates to a method where one or more solid objects of biological origin are analyzed with respect to presence and quantity of predefined structures in said object. Even more in particular, it relates to the diagnosis of disease or malfunction by analysis of presence and quantity of predefined structures in tissue from an organism.

BACKGROUND OF THE INVENTION

Analytical and diagnostic procedures are crucial in many functions in the modern society. One of the most common is the diagnostic procedures performed at health care institutions (e.g. hospitals) with the purpose to determine if a patient has a particular disease. For example, elevated concentration of the prostate specific antigen (PSA) in male blood is an indication of ongoing prostate cancer in the patient. However, this is not specific enough and there is need for better methods to analyze different modifications of PSA to improve the clinical decision based on analytical results. Other analytical or diagnostic procedures include, but are not limited to, the diagnosis of cancer based on ocular analysis of stained tissue biopsies, diagnostics of cattle prior to slaughter in order to produce safe food, diagnostic procedures in veterinary sciences with the purpose of treating sick animals, targeted radiotherapy of tumors in animal or humans, the detection of pathogens or toxins in food or feed stuff, the determination of the concentration of nutritional supplements (e.g. vitamins) in processed food or feed stuff, the detection of hazardous chemicals in the environment and the like.

Whenever the solid object structure is complex, most of the currently used methods must use reagents that are highly specific to amplify the signal from one component in the complex sample. Such complex structures can be cell surfaces on cells in tissue or in body fluids. Still other types of complex structures are or protein complex where the individual proteins change conformation or can be modified by posttranslational modifications.

One particular method for diagnosis is immunohistochemistry (IHC). Diagnostic IHC procedures are developed for a multitude of diseases, most notably for cancers. In brief, IHC is a method wherein a thin slice of tissue is placed onto a microscope glass slide followed by staining of selected receptors. An image is made of the stained tissue slice and a trained operator is judging if the tissue contains staining patterns indicative of disease. Even though IHC is used world-wide and has improved the possibility to diagnose serious diseases like cancer, general IHC methodology still suffers from poor repeatability and long tissue preparation protocols (as evident in the report "Current issues in ER and HER2 testing by IHC in breast cancer". by Allen M Gown published in Modern Pathology 2008 May; 21 Suppl 2:S8-S15, which is incorporated by reference herein).

Immunohistochemistry is one of the dominant methods for analysis of tissue slices. Being used in the majority of major hospitals, it is a well known method for persons skilled in the art of tissue analysis. In brief, IHC is a method for localizing proteins in cells of a tissue section by use of antibodies binding specifically to antigens in biological tissues. IHC staining is commonly used in the diagnosis of abnormal tissue such as tumors. Specific molecular structures on or in the cells in the tissue are characteristic of particular cellular events indicative of disease. In order to visualize the antibody-antigen interaction, the antibody can be tagged to a fluorophore, such as FITC, rhodamine, Texas Red or any other fluorescent moiety. In the procedure thin (typically 20 μm) slices are taken of the tissue of interest. The tissue is then treated to rupture the membranes, usually by using a detergent (e.g. Triton X-100). After these steps, the tissue slice is prepared for antibody treatment, which typically follows an indirect approach. The indirect approach involves a primary (unlabeled) antibody which reacts with tissue antigen, and a secondary (labeled) antibody which reacts with the primary antibody. The secondary antibody is normally labeled with a fluorescent moiety or an enzyme. IHC is a powerful detection technique and is capable of showing exactly where a given protein is located in the tissue sample. IHC is widely used in many fields of biology, e.g. in the neurosciences, enabling researchers to examine protein expression within specific brain structures and in diagnostic surgical pathology for typing tumors (e.g. carcinoma vs melanoma). The result of an IHC analysis is always an image of the tissue slice with areas containing certain targeted receptors stained in a distinguishable color. As such, IHC is an end-point measurement, i.e. it is only possible to detect the status of the antibody-antigen interaction at one point in time. IHC also suffers from the often manual interpretation of images; trained operators may disagree on the extent and intensity of the staining of the very same tissue slide, leading to uncertainties when comparing results across operators and laboratories. Another major disadvantage of IHC is that it is impossible to show in IHC that the staining corresponds with the protein of interest. A description of IHC used in clinical practice is available in the report "Diagnostic evaluation of HER-2 as a molecular target: an assessment of accuracy and reproducibility of laboratory testing in large, prospective, randomized clinical trials". By Press M F, Sauter G, Bernstein L, Villalobos I E, Mirlacher M, Zhou J Y, Wardeh R, Li Y T, Guzman R, Ma Y, Sullivan-Halley J, Santiago A, Park J M, Riva A, Slamon D J. Published in Clinical Cancer Research 2005 Sep. 15; 11(18):6598-607, which is incorporated by reference herein.

SUMMARY OF THE INVENTION

One object of the present invention is to facilitate the analysis or diagnosis of solid objects wherein said analysis comprises use of one or more probes that interacts with structures on said object. The invention is particularly useful for analysis of solid objects of biological origin through the use of probes of biological or chemical origin.

The invention relates in particular to an improved method of analysis or diagnosis of solid objects. The method is based on real-time detection of how predefined probes interact with structures present on or in the solid object combined with the calculation of how the recorded binding curves of said probes are distributed in terms of interaction properties. The distribution of interaction properties is used as a fingerprint of the solid object, and said fingerprint contains distinct features indicative of the status of the solid object. A classification algorithm is applied on the fingerprint to automatically determine status of the solid object. The method is particularly advantageous for solid biological objects like tissue slices combined with antibody probes, said antibody recognizing receptor structures known to be over-expressed in disease states on said tissue slice. This method would therefore improve commonly performed analytical and diagnostic procedures by using the information of how probes interact with solid surfaces to define the solid surface.

Therefore, in one aspect the invention provides an analytical method capable of classifying solid objects into predefined classes, such as malign/benign, good/bad prognosis of therapy, acceptable/unacceptable quality and the like.

The method comprises providing a solid support having a solid object attached thereon and a solution containing one or more probes, and detection both of the presence of interaction between probe and solid object and of the rate of formation of complexes of probe and solid object. The output from said detection is first transformed into a graph showing the amount of bound probe versus time, also known as a binding curve. Using the binding curves representing the probe-object interaction, the distribution of interaction properties is calculated. The distribution of interaction properties is used as a fingerprint of the solid object, said fingerprint carrying distinct features useful for establishing criteria for classifying the solid object as benign/malign, good/poor prognosis of therapy, acceptable/unacceptable quality and such. The method according to the invention is defined in claim 1.

Thus, the invention in a first aspect provides a method for measurement of properties of solid objects usable in analytical or diagnostic procedures, the method comprising providing one or more probes, said probe being capable of interacting with structures on the solid object in question to form probe-object complexes, attaching the solid object to a solid support; providing a solution of the probes of interest, bringing said solution in contact with the solid object attached to the support, detecting the presence of interaction between probe and solid object and the rate of formation of probe-object complexes to form a curve representing the amount of probe bound to the solid object over time; approximating said curve with a weighted sum of all primitive curves in a predefined set of primitive binding curves, calculating the weight of each primitive binding curve so that said weights minimizes the difference between the detected binding curve and the sum of weighted primitive binding curves; and classifying said solid object for use in an analytic or diagnostic procedure by using criteria based on said of weights, either alone or in combination with further data.

In a preferred embodiment the invention comprises that said detection is performed without bringing the detector in contact with said solid support.

In a still more preferred embodiment said detector is either a radioactivity detector or a fluorescence detector.

Suitably, the number of primitive binding curves and corresponding weights are at least nine.

In other embodiments said probes are selected from proteins, DNA, RNA, and organic compounds, said probes possibly being labelled with either a radioactive or fluorescent moiety.

Furthermore, said solid objects can be selected from objects of biological origin, or mammal tissue.

In a further aspect, the invention provides a method for diagnosing based on the result from an analysis according to the method defined in claim 1.

In yet a further aspect, the present invention also relates to a kit of probes usable for quality control or diagnosis of solid objects by use of the method according to the invention.

BRIEF DESCRIPTION OF THE DRAWINGS

The present invention will be disclosed in closer detail in the description and example below, with reference to the accompanying drawing, in which FIG. 1 a schematic representation of the method of the invention.

DETAILED DESCRIPTION OF THE INVENTION

For the purpose of the present application, and for clarity, the solid object under analysis is attached to a solid support and the predefined probes designed to interact with structures on the solid object are present in a liquid that is in contact with said solid support. Possible solid objects include, but are not limited to, tissue samples, embedded tissue samples and sections thereof, cells, bacteria, viruses, magnetic particles, surface coatings (e.g. paint), multi-cellular organisms (living or dead), material designed for implantation in organisms (e.g. titanium screws, ceramic plates and similar), or any combination thereof. A solid object is thinner than 10 mm, and is typically thinner than 1 mm. The solid object further has an area less than 100 $cm^2$, and typically said area is greater than 1 $mm^2$ and less than 10 $cm^2$.

The attachment of said solid object to said solid support is typically a strong attachment, like covalently bound proteins, adhesive cells grown on the solid support, or non-biological objects glued to the solid support to mention a few. It is however possible to use weakly attached solid objects, where the method of attachment is mediated through for example electrostatic interaction, hydrophobic interaction, and trapping of solid objects in high-viscosity gels to mention a few possibilities.

The probes used in this invention must have two characteristic properties: First, a probe has to attach to or interact with a structure which is searched for in the solid object under investigation. Second, it must be possible to detect, in a time resolved fashion, the probe interacting with said solid object. A typical probe for a biological object may be a protein known to specifically interact with a certain receptor, the presence of said receptors in the biological object being known in advance to be indicative of disease. Said probe may further have a fluorescent tag (e.g. FITC, Cy2, Cy3, Cy5, Texas Red, or any other fluorescent tag) attached for simple detection of the amount of probe bound to said biological object. Possible probes for use in analytical or diagnostic procedures include but are not limited to, macromolecules (e.g. proteins, DNA, RNA), antibodies, aptamers, affibodies, nanobodies, peptides and other chemical compounds and any species that can be dissolved in liquid or even cells, organelles, organisms or particles that can be suspended in a liquid. A requirement on the probe is that it can be dissolved or suspended in liquid and that it does not sediment within 24 hours (under influence of normal gravitation). The probe may have some sort of label attached. Suitable labels include, but are not limited to, radioactive labels and fluorescent labels.

The term primitive binding curve is in this context defined as a curve representing the course of binding according to a predefined interaction model, said primitive binding curve being calculated given a few (typically less than 10) interaction properties. An example of a family of primitive binding curves is the curves from a monovalent interaction model, wherein each primitive binding curve can be calculated given the association rate constant $k_a$, the dissociation rate constant $k_d$ and the signal at saturated solid support $R_{MAX}$.

The present invention also includes kits of probes or solid supports used for analytical or diagnostic procedures by the method.

Generally, the invention in its first aspect is based on the provision of five characteristic components. These five aspects are:
One or more probes suitable for an analytical or diagnostic measurement, possibly labeled with a detectable marker,
A solid object under study,
A time resolved measurement of the interaction between the probes and the solid object,
A method for representing the time resolved measurement, where said representation provides a multidimensional fingerprint of the nature of the interaction of the probe with the solid object.
Applying a classification algorithm on said fingerprint to obtain a statement on the status of the object.

The present invention aims i.a. at improving the classification of solid objects for use in analytical or diagnostic procedures by providing an interaction map as input for classical classification algorithms. In some analytical or diagnostic procedures, the difference between a favorable status of a solid object (e.g. acceptable quality or benign tumor) and an unfavorable status (e.g. inacceptable quality or malign tumor) is constituted by the relative fraction of related structures in the solid support. In oncology, over-expression of certain receptors is known indications of disease, which in fact is an alteration of the relative abundances of the receptor plethora of a cell. In drug discovery, the transport of potential drugs through the cell membrane in order to reach an intracellular target receptor is an important quality measure of both the potential drug and the cell culture or tissue used as solid object. In objects designed for implantation in human patients, the surface of the implanted object should be biocompatible. In other objects of non-biological origin, the surface porosity and the degree of oxidation of the surface may be integral for the quality or performance of the object.

Even though the invention is described as the analysis of binding events between a probe and a solid object, it is not necessary that the invention is used exclusively in that experimental set-up. It is, for example, possible to use a trace element, such as Chromium, as probe. The direct, real-time detection of $^{51}Cr$ in solid objects has been previously disclosed in WO2009029039, which is incorporated by reference herein. It is further possible to measure events of inherent origin of the solid object (such as the resistance, impedance or capacitance across a solid object) under the influence of a probe. For example, the change of impedance across a monolayer of cells over time can be measured with presence of different sugar molecules as energy supplement (e.g. fructose, sucrose, and glucose). In this case, the monolayer of cells is the solid object and the different sugar molecules are different probes.

Figure 1:
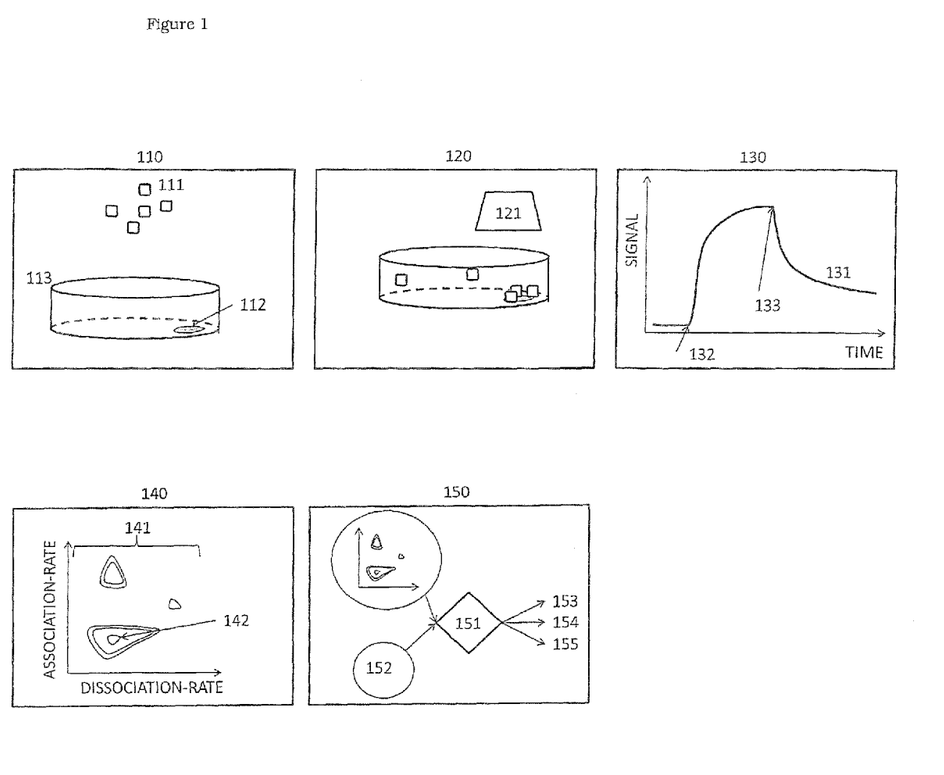

The method used for analytical or diagnostic purposes can be described as a five-step procedure which is outlined in FIG. 1. In the first step (110), a solid object (112) is attached to a solid support (113) and a suitable probe (111) dissolved in liquid is made available. In the second step (120), the liquid containing probe (111) is put in contact with the solid support (113) and the solid object (112). When the liquid is in contact with the solid support (113), a measurement device (121) is activated in order to measure the amount of probe (111) that has bound to the solid object (112). After a predetermined time, the liquid containing probe (111) may be replaced with liquid without probe. In the third step (130), the readings from the measurement device is presented as a binding curve (131) which shows both the presence of interaction between probe and solid object and the rate of formation of probe-object complexes as a curve representing amount of probe bound to the solid object over time. The time points for probe addition (132) and probe removal (133) are identified in the binding curves unless they are known in advance. In the fourth step (140), the measured binding curve (131) is expressed as a sum of a predefined set of primitive binding curves, each such primitive curve being multiplied with a weight to adjust the amplitudes of the different primitive curves in the sum that represents the measured binding curve (131). Thus, each measured binding curve (131) can be represented by a plurality of weights, each weight being associated to a primitive curve. Such a collection of weights is referred to as a vector of weights. Different measured binding curves will be expressed as different vectors of weights. In some cases, the vector of weights can in turn be presented as a topographic map, where the surface of triplets (typically [association rate, dissociation rate, weight]) is plotted as a contour plot (141). Each "hill" (142) in this plot means that the corresponding association and dissociation rate values have elevated weights, which means that the binding curve (131) is partly composed of an interaction of the corresponding association and dissociation rate values, which in turn means that the probe (111) is interacting with the structures of the solid object (112) with the corresponding association and dissociation rate values. In the case of biological objects, each probe-receptor interaction will result in at least one such "hill", and the locations and relative heights of the "hills" for a given biological object will represent the receptor expression concentration or status of the biological object. In the fifth step (150), said weights are fed into a classification algorithm (151), possibly together with further data (152). The classification algorithm may be a neural network, a linear discriminant classifier, a support vector machine, a k-nearest neighborhood classifier, or any other algorithm capable of classifying a set of input data into at least two different classes based on features in said input data. The output of the classification algorithm (151) is exemplified as three different classes (153, 154, 155), which for example could represent the classifications [healthy; uncertain; disease] of a tissue sample.

The solid object under investigation needs to be attached to a solid support. The method of attachment may differ depending on the type of solid object. Living or fresh biological objects may adhere spontaneously to certain plastic and glass surfaces, but in some cases the solid support has to be coated with certain proteins (like fibronectin, concavalin A, polylysine, or bovine serum albumin to mention a few) to facilitate adhesion. In case the solid object is paint or other protective surface coatings, they typically are inherently adhesive. Still other objects may be glued to the solid support.

The solid support used in the invention is a rigid structure, is typically made of glass or plastic, and is essentially flat. The support is normally designed in conjunction with the detection technology. Examples of solid supports include, but are not limited to, glass slides (e.g. microscope slides, microscope cover slides, glass slides covered with gold films designed for detection in surface plasmon resonance detectors, glass slides with a plurality of coatings of different refractive index for interferometric detection, and glass slides with an imprinted grating to mention a few), transparent plastic slides (plastic slides covered with gold films designed for detection in surface plasmon resonance detectors, plastic slides with a plurality of coatings of different refractive index for interferometric detection, and plastic slides with an imprinted grating to mention a few), and petri dishes made of either glass or plastic. The solid support may contain features that relates to the detection principle, including (but not limited to) a thin gold layer, an imprinted grating, embedded electrodes, and surface coating with enzymatic activity to mention a few.

Figure 2:
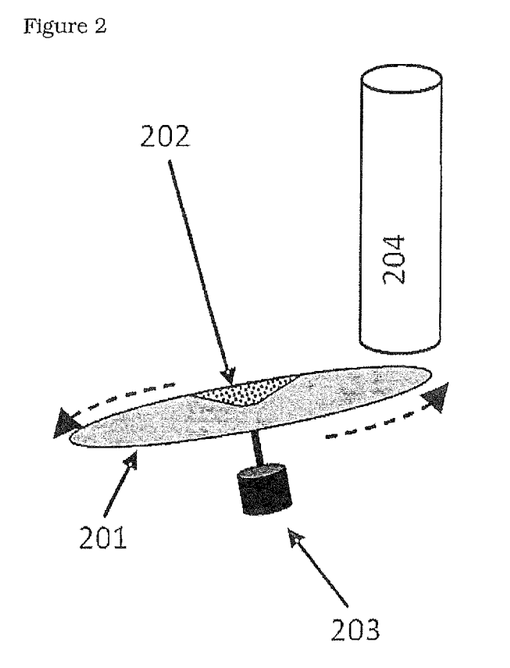
FIG. 2 shows a suitable instrument, known in prior art, for performing the measurement in the quality control method.

There are several methods available for the measurement of the rate of complex formation and the magnitude of formed complexes between a probe and the solid object. Methods based on surface plasmon resonance and similar techniques are available, as described in the report "Survey of the year 2006 commercial optical biosensor literature" by Rich R L and Myszka D G published in Journal of Molecular Recognition 2007 September-October; 20(5):300-66 (which is incorporated by reference herein). Time resolved confocal microscopy and similar imaging techniques are alternative methods, as described by Praus P, Kocisova E, Mojzes P, Stepanek J, Seksek O, Sureau F and Turpin P Y in the report "Time-resolved microspectrofluorometry and fluorescence imaging techniques: study of porphyrin-mediated cellular uptake of oligonucleotides". Published in Annals of the New York Academy of Sciences 2008; 1130:117-21 (which is incorporated by reference herein). A preferred method for completing step 120 in FIG. 1 has been previously disclosed [WO2005080967, which is incorporated by reference herein] and is schematically described in FIG. 2. In brief, the method relies on a solid object (202) being immobilized to a defined area on a solid support (201), denoted an "active area". On the same solid support, there is also a reference area (in this case opposite to the active area). A liquid containing a dissolved probe is in contact with the solid support to enable an interaction between object and probe. Furthermore, the solid support is inclined and slowly rotated using a motor (203). Over the elevated portion of the solid support, a detector capable of detecting the label attached to the probe used is mounted (204). Said detector is typically not in contact with the solid support, but registers e.g. emitted radiation of radioactive nuclides or emitted light from fluorescent labels. When the active area passes the detector, an elevated signal will be registered in case the ligand has bound to the target. For each rotation, a binding level value can be calculated by subtracting the detected signal from the reference area from the detected signal from the active area. When collecting binding level values from a series of rotations, a time resolved binding curve is obtained.

The detection method in this invention may have spatial resolution. For example, a high-resolution digital photograph of the solid object may be taken repeatedly during the course of the measurement. By dividing the picture of the object in different areas, it is possible to obtain one binding curve for each area in one measurement. Thus, given spatially resolved detection devices, this invention can be applied not only to complete solid objects, but also to selected parts of said objects. Spatially resolved detection is of particular interest for medical decisions when analyzing thin sections of tissue. Dependent on resolution several different tissue sections can be applied on one solid support in array like structures.

Figure 3:
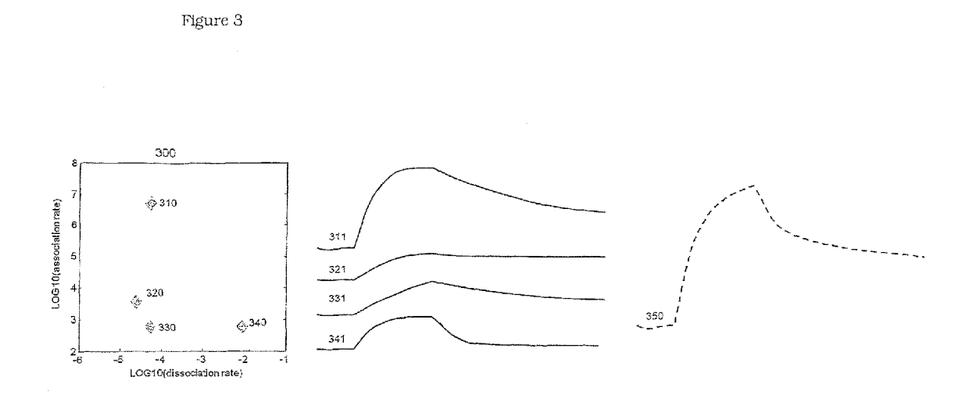
FIG. 3 illustrates the representation of a binding curve as an interaction map.

The representation of one or more binding curves by a sum of several primitive theoretical binding curves can be interpreted as briefly outlined in FIG. 3. Given a contour plot (300), similar to the one denoted 141 in FIG. 1, each "hill" is indicating that the primitive binding curve associated with the hill is present in the measured binding curve (350). In FIG. 3, the hill 310 has highest amplitude, as indicated by the number of contour lines. The corresponding primitive curve 311 is therefore the dominant contribution to the representation of the measured curve (350). The hill 320 is lower in amplitude, but also has slower association rate and slower dissociation rate. This means that the characteristic shape of the corresponding curve 321 is slower both for probe uptake and probe dissociation. In the representation of the measured curve (350), primitive curve 321 is a small contribution. Hills 330 and 340 have corresponding primitive curves 331 and 341 respectively, and these are added to the representation as described above. The measured curve 350 is thus represented by a sum of all primitive curves forming the basis of contour plot 300, wherein all weights are small except for the primitive curves 311, 321, 331 and 341 which are weighted according to interaction map 300.

The background of the representation outlined in FIG. 3 has been discussed in relation to optical biosensors in the report "Combined affinity and rate constant distributions of ligand populations from experimental surface binding kinetics and equilibria". by Svitel J, Balbo A, Mariuzza R A, Gonzales N R, and Schuck P published in Biophys J. 2003 June; 84(6):4062-77 (which is incorporated by reference herein). The idea resembles the expression of any curve as a sum of orthogonal polynomials, more known as an exchange of base. In the case of this invention, the primitive binding curves are typically selected from the class of monovalent interactions. The theoretical binding curve for such interaction models can be expressed analytically, as described by Khomyakova E, Livshits M A, Steinhauser M C, Dauphinot L, Cohen-Kaminsky S, Rossier J, Soussaline F, Potier M C. In the report "On-chip hybridization kinetics for optimization of gene expression experiments". Published in Biotechniques 2008 January; 44(1):109-17 (which is incorporated by reference herein).

In the case of probe—solid object interactions wherein one known concentration of probe is added at time point $t_{ass}$ and is replaced with liquid devoid of probe at time-point $t_{diss}$, a theoretical monovalent interaction model can be described according to:

$$Y=0 \text{ for } t<t_{ass}$$

$$Y=R_{MAX}*C/(C+k_d/k_a)*(1-\text{EXP}(k_a*C+k_d)*(t-t_{ass})) \text{ for } t_{ass} \leq t < t_{diss}$$

$$Y=R_0*\text{EXP}(-k_d*(t-t_{diss})) \text{ for } t \geq t_{diss}$$

Where $R_{MAX}$ is the signal obtained when all possible binding sites on the solid object has a probe bound to it, $k_a$ is the association rate constant of the interaction, $k_d$ is the dissociation rate constant of the interaction, $R_0$ is the Y value as time $t_{diss}$. Three parameters are known in advance: $t_{ass}$ is the time of probe addition, $t_{diss}$ is the time of probe removal, and C is the concentration of the probe.

The primitive binding curves can however be selected from any other class of interactions models, including (but not limited to) a monovalent interaction model with correction for diffusion limitation (also known as a correction for mass transport limitation), a monovalent interaction model with correction for depletion of the probe due to the interaction with the solid object, and a bivalent interaction model. In cases where the measurement of the status of the solid object is made using a probe that does not interact with the solid object (e.g. a trace element), other curves may be used as primitive curves, such as passive diffusion into different compartments of the solid object with or without active transport of the probe (e.g. by influx and efflux pumps in a cell membrane). In cases where the measurement of the status of the solid object is made without using a probe, still other curves may be used as primitive curves. Under all circumstances, all classes of primitive curves typically have less than 10 free parameters (e.g. diffusion constants and compartment volumes in the case of diffusion into different compartments).

It is possible to exemplify the use of primitive curves according to the theoretical monovalent interaction model for representation of the measured binding curve (131). The measured curve 131 is then approximated by $Y_{hat}$ which is a sum of several theoretical curves $Y_i$, i=1 . . . n each multiplied by corresponding weights $w_i$, i=1 . . . n, where n is the total number of predefined $[k_a, k_d]$ values used in the approximation.

$$Y_{hat} = \Sigma_{i=1\ to\ n}(w_i * Y_i)$$

Where $Yi=Y(k_{ai}, k_{di})$ for an arbitrary $R_{max}>0$, typically selected as $R_{max}=1$.

The weights $w_i$ are selected to minimize the value of a cost function. A common cost function is the sum of squared residuals, which is computed by first subtracting $Y_{hat}$ from the measured binding curve (131), then computing the square of each residual element, and finally summing all squared residual elements. The sum of squared residuals value will be small when $Y_{hat}$ closely resembles the measured binding curve (131).

There are automated methods for finding the weights $w_i$ by minimizing the value of the cost function. One such possible method is the method by Marquardt-Levenberg, as described by Carrot C, Guillet J, May J-F, and Puaux J-P in the report "Application of the Marquardt-Levenberg procedure to the determination of discrete relaxation spectra" published in Macromolecular Theory and Simulations 1(4):215-231, 2003 (which is incorporated by reference herein). Other possible methods include, but are not limited to, simplex optimization, genetic algorithms, and gradient based optimization algorithms.

When the weights have been calculated, it may be possible to plot the weights in a three-dimensional plot. Typically, the dissociation rate constants are assigned to the x-axis and the association rate constants are assigned to the y-axis. The weights are plotted in the z-direction, either as a colorimetric plot where e.g. a gradient from red to blue is used to represent weight values or as a contour plot (141) where higher weights are shown with iso-weight-level lines, much like a topographic map. Thus, this exemplary representation of the measured binding curve (131) by the use of primitive curves according to the theoretical monovalent interaction model a plurality of weights for the predefined values of $[k_a,k_d]$ used in the approximation.

In some cases the optimization problem may be underdetermined, i.e. there may be several different sets of $w_i$ that produces an $Y_{hat}$ that is equal to a measured binding curve (131). In such cases it is preferred to apply a regularization algorithm (e.g. Tichonov regularization) when searching for the set of $w_i$ that minimizes the difference between $Y_{hat}$ and the measured binding curve (131). In brief, a regularization algorithm adds penalty on sets of $w_i$ with high variance which leads to convergence towards the solution with the fewest number of large $w_i$ (which will also be the simplest of the possible solutions).

When using the interaction map for comparisons of different solid objects and/or different probes, it may be important to use the same predefined set of primitive curves when calculating the interaction maps for the cases subject to comparison. It may also be important to use the same initial value for the minimizing algorithm when calculating the interaction maps for the cases subject to comparison.

The benefit of using the method of this invention is that many probe-object interactions are of heterogenous nature, and the heterogeneity as such contains information about the distribution of similar structures in the solid object. For example, in case the solid object is a slice of tissue, cancerous cells in the tissue may express a certain receptor in abundant amounts and with mutations in the amino acid sequence of the receptor. A probe selected for such a receptor could be a monoclonal antibody labeled with a fluorescent moiety. The interaction of the antibody with the mutated receptor of the cancer cell will most likely be different to the interaction with the natural receptor. Since the tissue slice probably contains both cancerous and normal cells, the measured binding curve would reflect both the interaction with the mutant and the interaction with the normal receptors, and hence give rise to two peaks in the three-dimensional plot of weights. The relative height of the two peaks would further indicate the relative number of mutant and normal receptors.

Basically this invention makes it possible to measure the concentration of genetic variants of important proteins for e.g. cancer development and treatment. It can form the basis for measurements of biomarkers for personalized medicine in form of drug for treatment or labeled molecules for in-vivo imaging in individual patients. For example, the analysis of tissue from a patient using an antibody probe known to recognize receptor structures known to be over-expressed in disease states would result in a vector of weights which in turn can be used for classification of the tissue which enables making a decision of the status of said disease.

Genetic mutations of proteins in cell growth control systems are important for development of cancer. For example, genetic mutations in the gene expressing the protein P53 is common in many cancers. Other examples of changes in proteins are posttranslational modifications (e.g. glycosylation of proteins to mention one example) that give rise to closely related molecules that can be of significant biological importance. Such modifications are very difficult to analyze and mass spectrometry is currently one possible technology for such tasks. Antibody technology can be used for detection of mutations and posttranslational modifications, but antibody technology first requires precise knowledge of which mutation/translation to detect and second requires development of antibodies with very high specificity and large differences in affinity between closely related antigens. Developing such antibodies is difficult.

This invention makes it possible to identify closely related structures such as mutated proteins on or in the solid object. Probes that bind closely related structures (e.g. receptors with different mutations, to mention one example) with different kinetic properties can be used, because the time resolved detection combined with the fingerprint based on sums of weighted primitive curves can be used for identification of the structures in the solid support as well as quantification of the amount of the structures. Such defined probes are easier to develop because the requirements for difference between multiple binding structures are less stringent than for end-point based assays.

Closely related structures such as mutated proteins on or in the solid object may also be identified by use of affinity purified polyclonal antibody probes. Polyclonal antibodies are purified from an immunized animals serum and therefore typically contains several different antibodies binding do different immunogenic surfaces of the immunogen, hence the notation polyclonal. Such polyclonal antibodies can be purified to different degrees such as the Immunoglobulin fraction or affinity purified preparations on group specific ligands or the antigen itself. When using polyclonal antibodies as probe, the interaction will be inherently heterogenic, but all probes bind to the same receptor surface structure, albeit with different mechanisms. The likelihood that a small change in the receptor structure (e.g. mutation, conformational change, post-translational modification, phosphorylation, to mention a few of the modifications changing the molecular binding properties of the structure of the solid surface) will be detected is therefore higher when using polyclonal antibody probes, because only one of the several interactions relying on different mechanisms need to be altered due to the change in receptor structure. Such changes in the fingerprint of one or several "hills" can be correlated both to molecular properties or clinical predictions of effect of treatments or choice of molecules for in-vivo diagnostic imaging methods. It is further possible to mimic the properties of polyclonal antibody probes by mixing a number of known or unknown homogenous probes, for example by mixing five monoclonal antibodies known to bind to the same receptor, or by keeping a plurality of potential binders in the panning process when generating artificial binders (e.g. in phage display and similar methods). Other types of molecules such as parts of antibodies, scFv, nanobodies, affibodies, aptamers, peptides or any other molecule that can bind can be used in such mixtures.

Today, genetic variability is detected on DNA or RNA level in a cell. Using quantitative polymer chain reaction (PCR) techniques and related methods it is possible to detect such molecular species with high sensitivity. However, the cellular content of RNA is not a perfect mirror of proteins concentration, as discussed by Ellmark P, Hogerkorp C M, Ek S, Belov L, Berglund M, Rosenquist R, Christopherson R I, and Borrebaeck C A. in the report "Phenotypic protein profiling of different B cell sub-populations using antibody CD-microarrays" published in Cancer Letters 28; 265(1):98-106, 2008 (which is incorporated by reference herein). Also infectious agents can be determined e.g. virus strains with mutations in important virus defined proteins. This invention has the possibility to detect such differences by use of probes targeting the variable areas of the proteins expressed by frequently mutated genes. Identified interacting molecules in cellular networks are very useful as probes for identification of different binding properties in relevant binding or regulatory sites.

Any probe with two or more binding sites can be used and the invention makes it possible to distinguish between structures binding by one, two or more binding sites due to avidity effects. Of particular interest is the possibility to use bi- or multifunctional probes. Bifunctional probes can bind to two independent binding surfaces on the molecules forming the complex, and multifunctional probes can bind more than two independent binding surfaces. As the invention makes it possible to identify the contribution of mono and bivalent binding it is possible to quantify the content of closely distributed substances. This is of particular interest as many biological control pathways are consequences of formed molecular complexes.

When targeting structures with small differences, it may be that the two hills in a contour plot overlaps. In such cases, it can be advantageous to perform the measurement at elevated temperatures (i.e. at 37° C. instead at room temperature) because the thermodynamic properties of the probe-structure interaction may differ among the plethora of different structures. Another possibility is to perform the measurement in different environments in order to separate the normally overlapping hills. It is previously known that small changes in assay environment can impact interactions between one probe and similar structures, as reported by Andersson K, Choulier L, Hamalainen M D, van Regenmortel M H, Altschuh D, and Malmqvist M in "Predicting the kinetics of peptide-antibody interactions using a multivariate experimental design of sequence and chemical space" published in Journal of Molecular Recognition 14(1):62-71, 2001 (which is incorporated by reference herein). Therefore, by adapting the chemical environment of the measurement, overlapping hills may become separated which in turn may improve the analytical quality of the measurement. The same reasoning also applies to situations where more than one probe is used, and two probes interact with their respective targets with similar interaction properties.

This invention makes it possible to use mixtures of different probes. In such a case, each individual probe will have defined binding properties and will therefore contribute to the interaction with the structures on the solid object in a unique way. This makes it possible to multiplex the measurement. By using detectors that can separate the measured signal from different labels (e.g. radiation energy for different radioactive nuclides or different emission wavelengths for fluorescent labels to mention a few) a considerable multiplexing can be achieved. As each probe is predefined in its binding properties with structures on the solid support even probes in mixture with other labeled molecules can be identified and its contribution to the reaction on the solid support. In such cases the relative proportion of structures on the solid object and in the mixture of probes can be determined. This is of particular relevance when the mixture contains substances that unspecifically adsorb to any structure and wherein the adsorption process can be separated in the time resolved properties.

This invention also allows for the measurement of enzymatic activity on or in the solid object, for example by using a enzymatic substrate as probe. In cases where the substrate has defined properties and the enzymatic product formed is bound to structures on or in close vicinity of the solid object. This can be valid for functional enzymes as structures on the solid phase. If enzymes are used to detect binding of bifunctional probes combining binding with defined properties and enzymatic amplification of the binding by increased signal generation. Such enzyme products formed could be insoluble product or formation of a polymer with labels anchored to the surface to keep the product in close vicinity of the structure on the solid phase.

Example 1

In the following example, it is shown that small differences in probes applied on the same solid object may result in different interaction maps. The HNSCC cell line SCC-9 (obtained from American Type Culture Collection) was used as solid object. In brief, SCC-9 cells were cultured in complete medium at 37° C. in an atmosphere containing humidified air with 5% $CO_2$. The two probes in this example were the antibody cMAb U36 labeled with either $^{111}$In or $^{177}$Lu using the chelator CHXA"-DTPA. SCC-9 cells were grown on plastic petri dishes in a fashion suitable for measurement in LigandTracer Yellow (Ridgeview Instruments AB, Uppsala, Sweden), Radiolabeled antibody (1-15 µg) was added to the dish, and measurements started. In all cases, the binding curve was followed for at least four hours with presence of antibody and in some cases the liquid was replaced with pure medium to follow the wash-out phase of the interaction. Detailed instructions on cell culturing, antibody labeling, LigandCurver Yellow setup, and other practical issues are available in the report by Nestor M, Andersson K, Lundqvist H named "Characterization of $^{111}$In and $^{177}$Lu-labeled antibodies binding to CD44v6 using a novel automated radioimmunoassay". published in Journal of Molecular Recognition 2008 May-June; 21(3):179-83 (which is incorporated by reference herein).

Figure 4:
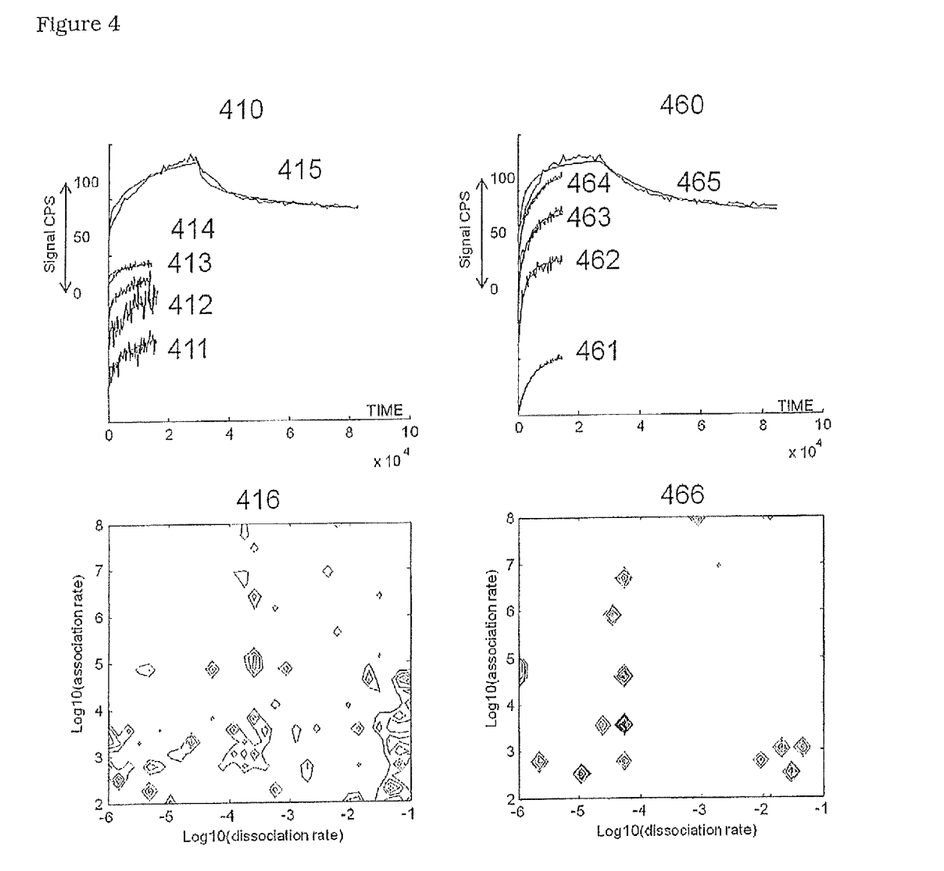
FIG. 4 shows a comparison of two interaction maps obtained for similar probes binding to the same solid object.

FIG. 4 shows the measured binding curves of the U36-$^{111}$In (410) and U36-$^{177}$Lu (460) probes binding to the SCC-9 object. In the case of U36-$^{111}$In (410), five individual curves were recorded with different concentration of U36-$^{111}$In: 1 µg/ml (411), 15 µg/ml (412), 10 µg/ml (413), 5 µg/ml (414), and 5 µg/ml (415). Furthermore, measurement 415 contained a wash-out phase, wherein the probe was removed at a certain point in time and the release of probe was measured. In the case of U36-$^{177}$Lu (460), five individual curves were recorded with different concentration of U36-$^{177}$Lu: 15 µg/ml (461), 10 µg/ml (462), 5 µg/ml (463), 1 µg/ml (464), and 5 µg/ml (465). Furthermore, measurement 465 contained a wash-out phase, wherein the probe was removed at a certain point in time and the release of probe was measured. In both plots of binding curves in FIG. 4, the individual measured curves have been shifted in the y-direction for enhanced visibility. Furthermore, both the measured curve (noisy line) and the representation in terms of summed primitive curves (smooth line) are shown.

The measured binding curves were imported into MATLAB 6.5 (The Mathworks, Natick, Mass.) and weights for 720 different primitive curves belonging to the monovalent interaction family were calculated using a sum-of-squared-residuals cost function and a simplex optimization method. The resulting weights were plotted as a contour plot with the logarithm of the dissociation rate constant $k_d$ on the x-axis, the logarithm of the association rate constant $k_a$ on the y-axis and the weight value as z-axis shown as contour lines. The contour plot for U36-$^{111}$In (416) is different from the one for U36-$^{177}$Lu (466), in particular in the region $-5<\log 10$(dissociation rate)$<-3$. U36-$^{111}$In (416) has a few high hills with log 10(dissociation rate)$\approx-4.2$ while as U36-$^{177}$Lu (466) has scattered hills with log 10(dissociation rate)$\approx-3.5$ to $-4$. This illustrates that small differences in probe design are visible even without a classification algorithm.

Example 2

Figure 5:
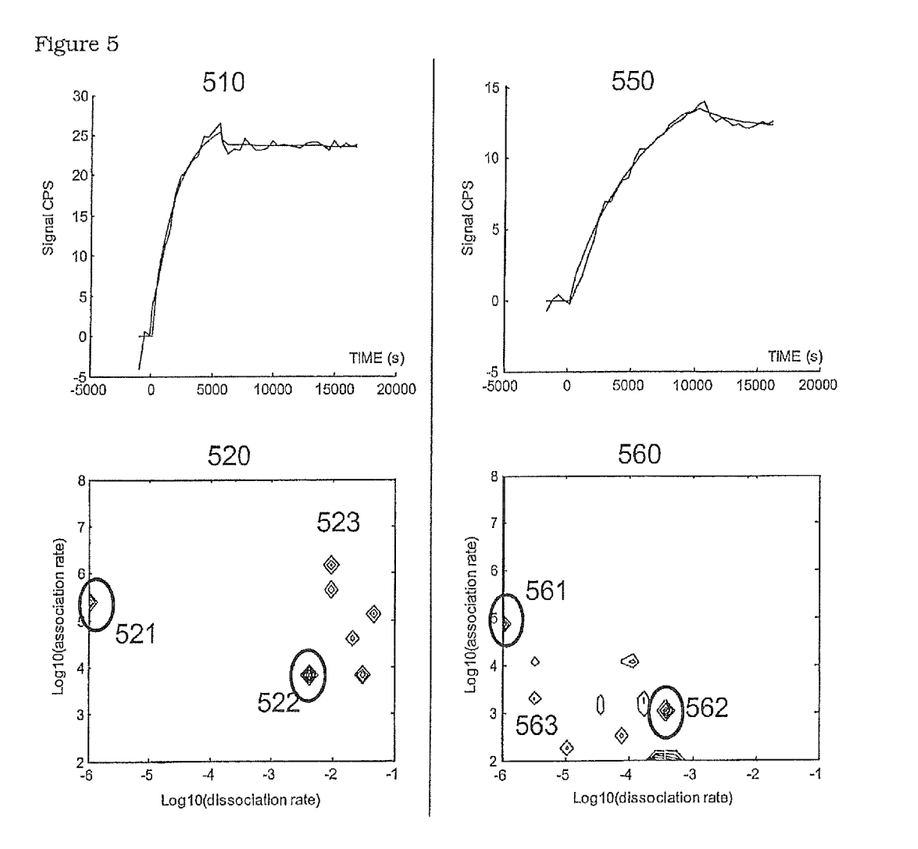
FIG. 5 shows a comparison of two interaction maps obtained for the same probe binding to similar solid objects.

In the following example, it is shown that small differences in solid object may result in different interaction maps when applying the same probe. The cell lines SKBR-3 and SKOV-3 (obtained from American Type Culture Collection) were used as solid objects. In brief, the cells were cultured in complete medium at 37° C. in an atmosphere containing humidified air with 5% $CO_2$. The probe in this example was the antibody trastuzumab labeled with the fluorescent marker AlexaFluo488. Trastuzumab is known to bind to the receptor HER2, and the cell lines SKOV-3 and SKBR-3 are known to express such receptors. Cells were grown on plastic petri dishes in a fashion suitable for measurement in a LigandTracer Green prototype (Ridgeview Instruments AB, Uppsala, Sweden). After a short baseline reading, fluorescently labeled antibody was added to the dish, and measurements started. In all cases, the binding curve was followed for at least one hour with presence of antibody after which the liquid was replaced with pure medium to follow the wash-out phase of the interaction. The resulting binding curves were imported into MATLAB and processed as described in example 1. Resulting curves and contour plots are shown in FIG. 5. Graph 510 shows the measured binding curve of trastuzumab—HER2 on SKBR-3 cells (noisy curve) and the sum of primitive curves (smooth curve) representing the measured curve. The weights used in the sum of primitive curves are shown in contour plot 520. Two dominant hills are seen in plot 520, one representing strong interaction (521) and one representing a weak and rapidly dissociating interaction (522). A few low hills (523) are also seen, but the low magnitude of the hills 523 makes them less important.

Graph 550 shows the measured binding curve of trastuzumab HER2 on SKOV-3 cells (noisy curve) and the sum of primitive curves (smooth curve) representing the measured curve. The weights used in the sum of primitive curves are shown in contour plot 560. Two dominant hills are seen in plot 560, one representing strong interaction (561) and one representing a weak and rapidly dissociating interaction (562). A few low hills (563) are also seen, but the low magnitude of the hills 563 makes them less important.

When comparing graphs 520 and 560, the dominant peaks are in slightly different positions. The strong component for SKBR-3 (521) has higher association rate than the strong component for SKOV-3 (561). Furthermore, the weaker components have approximately the same affinity, but the SKBR-3 (522) weak component has more fast on-fast off characteristics than the SKOV-3 weak component (562). Such subtle differences may be due to the overall receptor environment in the cell membrane or to alterations in the homo and heterodimerization balance in the different cell types. It should also be noted that SKBR-3 is derived from a breast cancer tumor while as SKOV-3 is derived from an ovarian cancer tumor, which can influence the expression pattern and post-translational modification routes of the HER2 receptor.

The difference in HER2 response to the selected probe in this example could have clinical consequences. In such cases, the optimal dosage or therapy or other clinical consequence would be decided by first determining the positions of the two dominant peaks for an unknown solid object and second comparing the detected peak positions with a set of predefined positions, each predefined position being associated with a suggested clinical consequence.

Example 3

Figure 6:
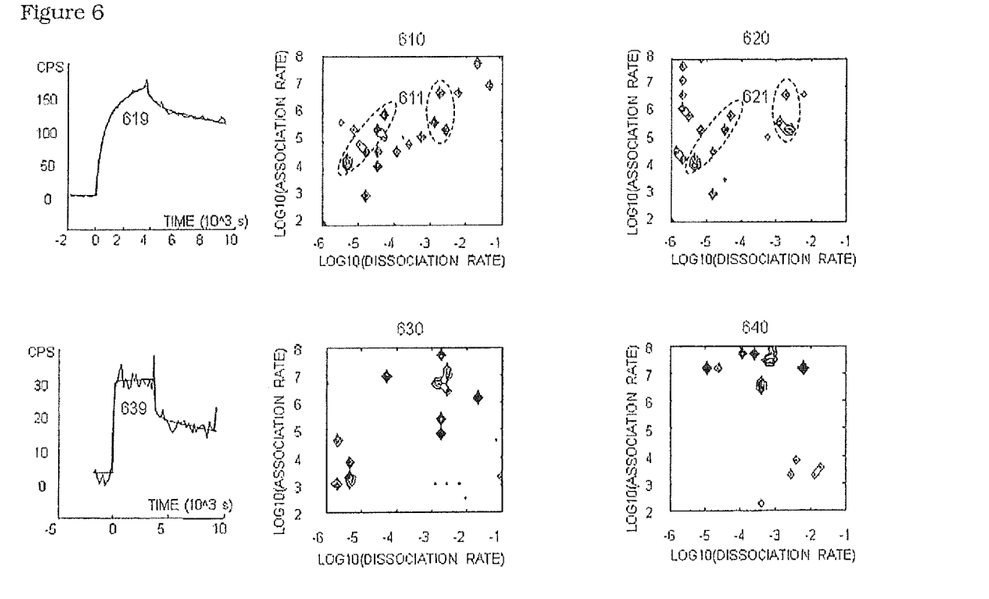
FIG. 6 shows a comparison of four interaction maps obtained for the same probe binding to similar solid objects.

In the following example, it is shown that small differences in solid object may result in different interaction maps when applying the same probe. The cell lines SKBR-3, and A431 (obtained from American Type Culture Collection) were used as solid objects. In brief, the cells were cultured in complete medium at 37° C. in an atmosphere containing humidified air with 5% $CO_2$. The probe in this example was epidermal growth factor (EGF) labeled with iodine-125. EGF is the ligand of the epidermal growth receptor (EGFR). It is known that A431 expresses large amounts of EGFR, and SKBR-3 may express EGFR but to a significantly lower degree. Cells were grown on plastic petri dishes in a fashion suitable for measurement in a LigandTracer Grey (Ridgeview Instruments AB, Uppsala, Sweden). After a short baseline reading, 1 nM radiolabeled EGF was added to the dish, and measurements started. In all cases, the binding curve was followed approximately one hour with presence of radiolabeled EGF after which the liquid was replaced with pure medium to follow the wash-out phase of the interaction. The resulting binding curves were imported into MATLAB and processed as described in example 1. These measurements were conducted twice for both cell lines A431 and SKBR-3. Resulting contour plots are shown in FIG. 6. The contour plot 610 shows the interaction map from one of the A431 measurements. This interaction proved to be of complex nature, because 7 dominant hills were identified, as indicated by the dashed circles (611). The corresponding binding curve 619 shows that the recorded binding signal was approximately 160 counts per seconds (CPS). The measurement was repeated using a new A431 cell dish, which resulted in the contour plot 620, in which the seven-peak pattern is visible (highlighted by dashed circles 621). The contour plot 630 shows the interaction map from one of the SKBR-3 measurements. There is no clear evidence that the recorded interaction is similar to the one for A431 cells, because the seven-peak pattern is missing. The corresponding binding curve 639 has a binding level of approximately 30 CPS. The second measurement of radiolabeled EGF binding to SKBR-3 cells resulted in contour plot 640, which also lack the seven-peak pattern. Since it is well-known that A431 cells express EGFR to a high degree, the large recorded binding signal resulting in the seven-peak pattern in plots 610 and 620 is likely indicative of a strong EGF-EGFR interaction. The other cell-line SKBR-3 known not to express large amounts of EGFR (if any) showed much lower recorded signal and clearly different contour plots (630,640), leading to the conclusion that either radiolabeled EGF binds to small amounts of EGFR on SKBR-3 in a completely different fashion than for EGFR on A431, or radiolabeled EGF binds to something else present on the SKBR-3 cell surface.

Example 4

Figure 7:
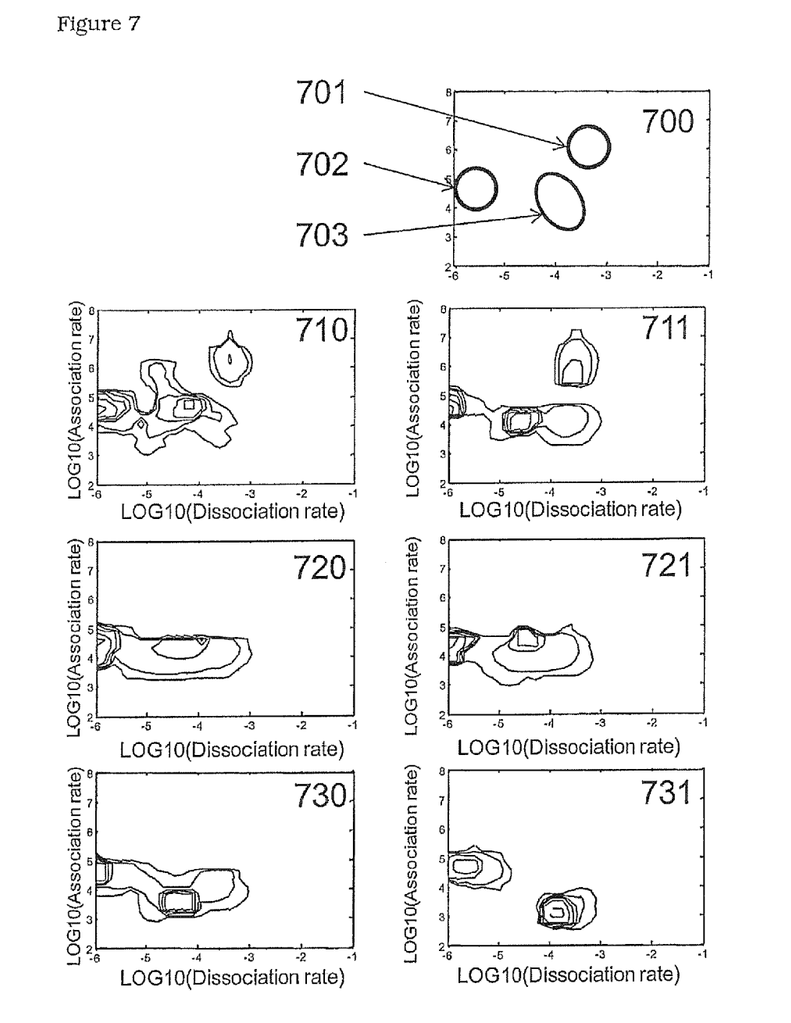
FIG. 7 shows a comparison of six interaction maps obtained for the same probe binding to similar solid objects.

In the following example, it is shown that small differences in solid object may result in different interaction maps when applying the same probe. The cell line A431 (obtained from American Type Culture Collection) was used as solid objects. In brief, the cells were cultured in complete medium at 37° C. in an atmosphere containing humidified air with 5% $CO_2$. The cells were grown in three different conditions: complete cell culture medium (HAMS-F10+10% fetal calf serum), complete cell culture medium supplemented with glucose (1 g/L), and cell culture medium without FCS. The probe in this example was the antibody cetuximab labeled with iodine-125. Cetuximab is known to bind to the receptor EGFR, and A431 cells are known to express such receptors. Cells were grown on plastic petri dishes in a fashion suitable for measurement in a LigandTracer Grey (Ridgeview Instruments AB, Uppsala, Sweden). After a short baseline reading, 4.4 nM radiolabeled cetuximab was added to the dish, and measurements started. In all cases, the binding curve was followed approximately two hours with presence of radiolabeled cetuximab after which the liquid was replaced with pure medium to follow the wash-out phase of the interaction. The resulting binding curves were imported into MATLAB and processed as described in example 1. These measurements were conducted twice for each growth condition. Resulting contour plots are shown in FIG. 7. The schematic plot 700 shows three regions in the interaction map where the cetuximab-EGFR interaction results in dominant hills. Region 701 corresponds to a rapid interaction component with a life-time of approximately 10 minutes. Region 702 corresponds to a slow (i.e. many hours) and strong component. Region 703 represents a weak component that requires higher concentration of the probe to be visible (when compared to 701 and 702). The other six interaction maps contain results from two independent measurements with A431 cells cultured in complete cell culture medium (710, and 711), from two independent measurements with A431 cells cultured in complete cell culture medium supplemented with glucose (720, and 721), and from two independent measurements with A431 cells cultured in cell culture medium without fetal calf serum (730, and 731). The interaction with complete medium (710, 711) has hills in all three regions (701, 702, 703). The hills in regions 702 and 703 have approximately the same magnitude and the hill in region 701 is less prominent. The interaction with glucose supplemented medium (720, 721) has hills in regions 702 and 703. The hill in region 702 has higher magnitude than the hill in region 703. The interaction with starvation medium (730, 731) also has hills in regions 702 and 703, but the hill in region 703 has higher magnitude than the hill in region 702. Thus, by use of interaction maps it is possible to differentiate between similar solid objects. It is further possible that the interaction maps reveal biological information that could be of interest. For example, it is known that the EGFR receptor forms dimers in the cell membrane, both with itself (homodimers) and with related receptors (heterodimers). One hypothesis is that the three regions 701, 702 and 2703 in fact represent the monomeric EGFR, homodimeric EGFR and heterodimeric EGFR.

Although the invention has been described with regard to its preferred embodiment, which constitute the best mode currently known to the inventor, it should be understood that various changes and modifications as would be obvious to one having ordinary skill in this art may be made without departing from the scope of the invention as set forth in the claims appended hereto.

The invention claimed is:

1. A method for measurement of properties of solid objects usable in analytical or diagnostic procedures, the method comprising:
    providing one or more probes, said probe being capable of interacting with structures on the solid object in question to form probe-object complexes;
    attaching the solid object to a solid support;
    providing a solution of the probes of interest;
    bringing said solution in contact with the solid object attached to the support,
    detecting the presence of interaction between probe and solid object and the rate of formation of probe-object complexes to form a curve representing the amount of probe bound to the solid object over time;
    approximating said curve with a weighted sum of all primitive curves in a predefined set of primitive binding curves,
    calculating the weight of each primitive binding curve so that said weights minimizes the difference between the detected binding curve and the sum of weighted primitive binding curves; and
    classifying said solid object for use in an analytic or diagnostic procedure by using criteria based on said weights, either alone or in combination with further data.

2. The method as claimed in claim wherein said detection is performed without bringing the detector in contact with said solid support.

3. The method as claimed in claim 1p wherein said detector is either a radioactivity detector or a fluorescence detector.

4. The method as claimed in claim 1, wherein the number of primitive binding curves and corresponding weights are at least nine.)

5. The method as claimed in claim 1 wherein the step of detecting interactions between probe in solution and solid object on a solid support, further comprises
immobilizing the solid object on a selected portion of the solid support;
reducing the amount of solution covering the selected portion of the support prior to performing said measurement; and
performing a reference measurement on a portion of said support where no interaction takes place.

6. The method as claimed in claim 5, wherein a difference between detection and reference measurements is calculated.

7. The method as claimed in claim 1, wherein the solid support is an essentially flat dish capable of holding a solution confined within its boundaries.

8. The method as claimed in claim 5, wherein the reduction of the amount of solution is achieved by orienting the support at an angle that deviates from the horizontal to provide an elevated part and a lower part of said support, such that the elevated part will be covered by less solution than the lower part, and wherein the support is rotated at a predetermined. speed of rotation.

9. The method as claimed in claim 1, wherein one member of the complex formed is labelled with a marker, such as radioactive marker or a fluorescent marker.

10. The method as claimed in claim 1, wherein said probes are selected from proteins, DNA, RNA, and organic compounds, said probes possibly being labelled with either a radioactive or fluorescent moiety.

11. The method as claimed in claim 1, wherein said solid objects are selected from objects of biological origin, or mammal tissue.

12. A method of diagnosing comprising performing a method as claimed in claim 1, wherein the solid biological objects are tissue slices combined with protein probes, said protein recognizing receptor structures known to be overexpressed in disease states on said tissue slice, and wherein the result of the classification is used for making a decision of the status of said disease.

* * * * *

UNITED STATES PATENT AND TRADEMARK OFFICE
CERTIFICATE OF CORRECTION

| | | |
|---|---|---|
| PATENT NO. | : 8,709,828 B2 | Page 1 of 1 |
| APPLICATION NO. | : 13/049316 | |
| DATED | : April 29, 2014 | |
| INVENTOR(S) | : Andersson et al. | |

It is certified that error appears in the above-identified patent and that said Letters Patent is hereby corrected as shown below:

In the Claims:

From line 63, column 16 to line 4, column 17, please correct claim dependencies and remove extra parenthesis in claim 2-5, in order to have claims 2-5 read in its entirety as follows:

--2. The method as claimed in claim 1, wherein said detection is performed without bringing the detector in contact with said solid support.

3. The method as claimed in claim 1, wherein said detector is either a radioactivity detector or a fluorescence detector.

4. The method as claimed in claim 1, wherein the number of primitive binding curves and corresponding weights are at least nine.

5. The method as claimed in claim 1, wherein the step of detecting interactions between probe in solution and solid object on a solid support, further comprises:
   immobilizing the solid object on a selected portion of the solid support;
   reducing the amount of solution covering the selected portion of the support prior to performing said measurement; and
   performing a reference measurement on a portion of said support where no interaction takes place.--

Signed and Sealed this
Fourth Day of August, 2015

Michelle K. Lee
*Director of the United States Patent and Trademark Office*